United States Patent
Chayet et al.

(10) Patent No.: US 10,058,454 B2
(45) Date of Patent: Aug. 28, 2018

(54) VISUAL AID PROJECTOR FOR AIDING THE VISION OF VISUALLY IMPAIRED INDIVIDUALS

(71) Applicant: IC INSIDE LTD, Tel Aviv (IL)

(72) Inventors: Haim Chayet, Nes Ziona (IL); Boris Greenberg, Tel Aviv (IL); Lior Ben-Hur, Tel Aviv (IL)

(73) Assignee: IC INSIDE LTD., Tel Aviv (IL)

( * ) Notice: Subject to any disclaimer, the term of this patent is extended or adjusted under 35 U.S.C. 154(b) by 219 days.

(21) Appl. No.: 14/423,668

(22) PCT Filed: Aug. 19, 2013

(86) PCT No.: PCT/IL2013/050702
§ 371 (c)(1),
(2) Date: Feb. 24, 2015

(87) PCT Pub. No.: WO2014/030158
PCT Pub. Date: Feb. 27, 2014

(65) Prior Publication Data
US 2015/0238362 A1   Aug. 27, 2015

Related U.S. Application Data

(60) Provisional application No. 61/693,247, filed on Aug. 24, 2012.

(51) Int. Cl.
| | |
|---|---|
| *H04N 1/195* | (2006.01) |
| *H04N 9/31* | (2006.01) |
| *A61F 9/08* | (2006.01) |
| *G02B 26/00* | (2006.01) |
| *G02B 27/00* | (2006.01) |

(Continued)

(52) U.S. Cl.
CPC .............. *A61F 9/08* (2013.01); *G02B 26/0833* (2013.01); *G02B 26/10* (2013.01); *G02B 26/101* (2013.01); *G02B 27/0093* (2013.01); *G02B 27/0101* (2013.01); *G02B 27/017* (2013.01); *G02B 27/104* (2013.01); *H04N 3/08* (2013.01); *H04N 9/3188* (2013.01); *G02B 2027/014* (2013.01); *G02B 2027/0118* (2013.01); *G02B 2027/0138* (2013.01); *G02B 2027/0141* (2013.01); *G02B 2027/0178* (2013.01)

(58) Field of Classification Search
CPC ..... A61F 9/08; G02B 27/017; G02B 27/0101; G02B 26/101; G02B 27/0093; G02B 27/104; G02B 26/0833; G02B 2027/014; G02B 2027/0118; G02B 2027/0141; G02B 2027/0178; G02B 26/10; G02B 2027/0138; H04N 9/3188; H04N 3/08
USPC ............................................................ 348/63
See application file for complete search history.

(56) References Cited

U.S. PATENT DOCUMENTS

| | | |
|---|---|---|
| 5,233,373 A | 8/1993 | Peters |
| 5,396,303 A | 3/1995 | Peters et al. |

(Continued)

FOREIGN PATENT DOCUMENTS

WO   2010062481 A1   6/2010

*Primary Examiner* — Jay Patel
*Assistant Examiner* — Salame Amr
(74) *Attorney, Agent, or Firm* — Reches Patents

(57) ABSTRACT

An apparatus, system or method for aiding the vision of visually impaired individuals having a retina with reduced functionality, which overcomes the drawbacks of the background art by overcoming such reduced and/or uneven retinal function.

12 Claims, 12 Drawing Sheets

(51) Int. Cl.
*G02B 26/10* (2006.01)
*G02B 27/01* (2006.01)
*H04N 3/08* (2006.01)
*G02B 26/08* (2006.01)
*G02B 27/10* (2006.01)

(56) References Cited

U.S. PATENT DOCUMENTS

| | | | |
|---|---|---|---|
| 5,653,751 | A | 8/1997 | Samiy |
| 7,023,621 | B2 | 4/2006 | Dietrich |
| 2002/0109819 | A1 | 8/2002 | Tuval |
| 2004/0136570 | A1* | 7/2004 | Ullman ............... G09B 21/008 382/114 |
| 2006/0039056 | A1* | 2/2006 | Lee .................... G02B 26/0816 359/212.1 |
| 2010/0149073 | A1* | 6/2010 | Chaum ............... G02B 27/0093 345/8 |
| 2011/0299034 | A1* | 12/2011 | Walsh .................. A61B 3/102 351/206 |
| 2012/0249988 | A1* | 10/2012 | Runde ................. G03F 7/70108 355/67 |
| 2012/0303092 | A1* | 11/2012 | Nanduri ............. A61N 1/36046 607/54 |

\* cited by examiner

Retinal FOV Segmentation with Associated Sensitivity Scores

Retinal Sensitivity Table

|  | 1 | 2 | 3 | 4 | 5 | 6 | 7 | 8 | 9 | 10 | 11 |
|---|---|---|---|---|---|---|---|---|---|---|---|
|  |  | Column number → |  |  |  |  |  |  |  |  |  |
| 1 | 1 | 1 | 1 | 1 | 1 | 1 | 1 | 1 | 1 | 1 | ... |
| 2 | 1 | 1 | 1 | 1 | 1 | 3 | 2 | 1 | 1 | 1 | ... |
| 3 | 1 | 1 | 2 | 2 | 4 | 5 | 4 | 2 | 1 | 1 | ... |
| 4 | 1 | 2 | 4 | 4 | 5 | 6 | 6 | 3 | 1 | 1 | ... |
| 5 | 1 | 2 | 2 | 3 | 8 | 8 | 5 | 2 | 1 | 1 | ... |
| 6 | 1 | 2 | 2 | 5 | 16 | 16 | 4 | 2 | 2 | 1 | ... |
| 7 | 1 | 1 | 2 | 6 | 5 | 7 | 3 | 2 | 1 | 1 | ... |
| 8 | 1 | 2 | 3 | 4 | 4 | 3 | 2 | 1 | 1 | 1 | ... |
| 9 | 1 | 2 | 1 | 2 | 2 | 2 | 2 | 1 | 1 | 1 | ... |
| 10 | 1 | 1 | 1 | 1 | 1 | 1 | 1 | 1 | 1 | 1 | ... |
| 11 | ... | ... | ... | ... | ... | ... | ... | ... | ... | ... |  |

(Row number ↓)

VISUAL AID PROJECTOR FOR AIDING THE VISION OF VISUALLY IMPAIRED INDIVIDUALS

FIELD OF THE INVENTION

The present invention relates to an apparatus, a system and a method for aiding the vision of visually impaired individuals, and in particular, to such an apparatus, system and method which assists visually impaired individuals having a retina with reduced functionality.

BACKGROUND OF THE INVENTION

Visually impaired individuals frequently suffer from reduced vision due to reduced functionality of their retina. Such reduced functionality may be due to damage, and/or to various disease processes which gradually reduce the function of the retina and hence lead to impaired vision over time. One example of such a disease process relates to AMD, or age-related macular degeneration, the leading cause of blindness among adults in the US. The macula is the part of the retina which provides sharply focused images and hence is particularly required for such activities as reading and driving.

AMD poses another challenge, which is that since its effects on the retina are uneven, mainly affecting the macula, such that assistive or corrective devices need to be able to relate to uneven retinal function, which may further vary between individuals. Currently, the most effective devices have involved implants to the eye, but these devices are highly experimental, very invasive and clearly undesirable (from a therapeutic standpoint) in many ways.

Various devices have been proposed which project light directly onto the retina, as disclosed for example in U.S. Pat. No. 5,653,751. However, the described device requires that an optical element be implanted into the eye, which again is highly undesirable as described above.

Some taught devices do not require any implantable element, as described for example in U.S. Pat. No. 7,023,621 to Dietrich; however this device assumes an ideal retina, with entirely homogenous functioning over the entire retina. For a normal, healthy retina, such an assumption, while incorrect, may still yield a reasonably effective device; however, for a retina with reduced function, or otherwise uneven function, such an assumption is not correct and greatly reduces the effectiveness of the device.

SUMMARY OF THE INVENTION

The background art does not teach or suggest an apparatus, system or method for aiding the vision of visually impaired individuals having a retina with reduced functionality.

By "reduced functionality" it is meant that the retina functions at a lower or lesser level than for a normal healthy retina, and/or that the retina has uneven function at different locations, so that for example and without limitation, one or more parts of the retina at different locations may function at a higher level, while one or more other parts of the retina, at other locations, may function at a lower level.

By contrast, the present invention is of an apparatus, system or method for aiding the vision of visually impaired individuals having a retina with reduced functionality, which overcomes the drawbacks of the background art by overcoming such reduced and/or uneven retinal function.

In at least some embodiments, the system of the present invention comprises a mapping unit, for mapping the retinal function at various locations of the retina; and a projection unit for projecting light onto the retina as a video projector, in which the location and/or intensity of the light at various parts of the retina is determined at least in part by the mapped retinal function. Optionally, both units may be implemented in a single apparatus; the mapping software and analysis functions may also optionally be implemented in that apparatus or alternatively may be implemented at a remote location. Communication between such a remote location and the apparatus may optionally be wireless or wired, as necessary.

According to at least some embodiments of the present invention, the level of retinal function at each of a plurality of portions of the retina determines whether that portion of the retina is stimulated through the video projection process or alternatively whether that portion of the retina is avoided during the video projection process; for the latter situation, the video data is projected onto the "remapped" retina, in which excessively low function portions of the retina are not stimulated but instead are avoided, as described in greater detail below. Optionally, this division between "stimulation" and "avoidance" may be implemented flexibly, according to the overall light level available, the type of vision desired (reading, driving, night vision) and so forth.

According to at least some embodiments of the present invention, in order to compensate for movement of the eye, the apparatus further comprises an eye tracker.

BRIEF DESCRIPTION OF THE DRAWINGS

FIG. 6 is an example of the first 10 rows by 10 columns of an illustrative RRST, for a retina which demonstrates reduced sensitivity within the center of this region;

DESCRIPTION OF PREFERRED EMBODIMENTS

Photons from a light source are modulated with video information by an intensity modulator. The modulated light is scanned in a first direction and in a second direction generally perpendicular to the first direction by a scanners to create a raster of photons that is projected directly onto the retina of the user by projection optics to produce the perception an image without any intermediate image outside of the eye that is viewed or perceived by the user. It is desirable to employ an eye tracking system to reposition the scanned raster of light as the pupil of the eye moves so that the light ray bundles are coincident with the entrance pupil of the eye.

The light source can be a monochromatic light or beams of red, green and yellow or blue light may be RGB video signals to scan colored photons directly onto the user's eye.

Figure 1:
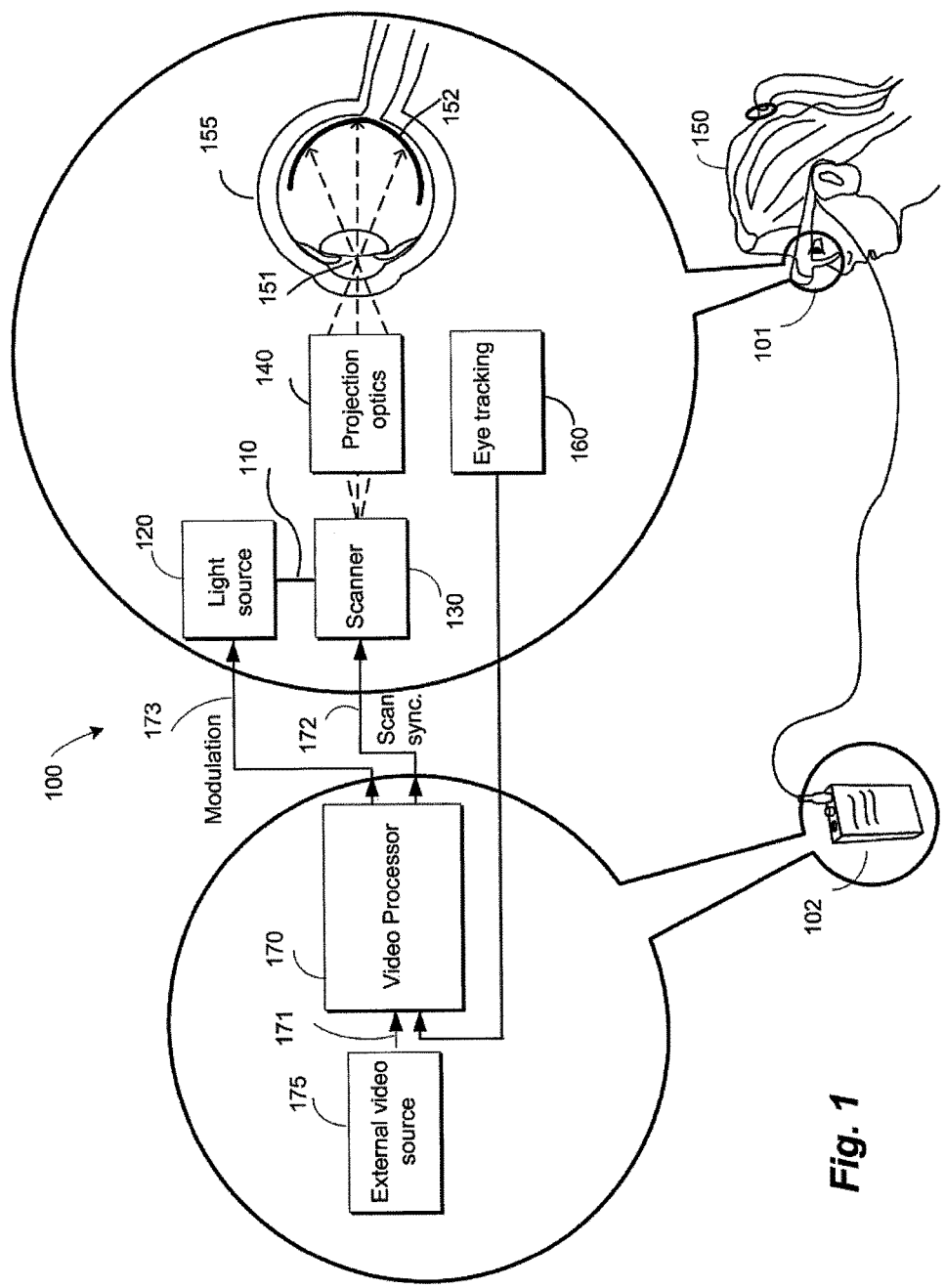
FIG. 1 shows a virtual retinal display (VRD) according to at least some embodiments of the present invention that projects a direct video image onto the user's retina.

Turning now to the drawings, a virtual retinal display (VRD) according to at least some embodiments of the present invention as shown in FIG. 1 projects a direct video image onto the user's retina.

The VRD 100 utilizes a light beam 110 emitted by a light source(s) 120, an optical scanner 130 that scans the light beam 110 in a raster mode horizontally and vertically, and is further relayed by projection optics 140 through the pupil 151 of user's eye 155 directly on the retina 152. A video processor 170 accepts an external video signal 171 from an external video source 175 and processes signal 171 in accordance with aspects of mapping as described in greater detail below, and optionally and preferably also according to the instantaneous position of pupil 151 as optionally and more preferably detected by an eye tracking system 160. The video processor 170 then generates a synchronization signal 172 to the scanner 130, and a modulation signal 173 according which light beam 110 is intensity modulated. The intensity modulated beam of light 110 as emitted from scanner 130 through optics 140 raster scans the retina 152 and so produces the perception of an image without any intermediate image outside of the eye 155.

Since the image is formed directly on the retina, without any intermediate displays or projection screens, the device can be reduced in size and weight, which in turn makes VRD 100 suitable for mounting onto head 150 of the user. However in any case it should be noted that VRD 100 as described herein is not intended for implantation to the eye 155 or attachment to the eye 155 and instead remains outside of the eye 155; only the intensity modulated beam of light enters the eye 155.

As seen in FIG. 1 VRD 100 preferably features a head-mounted part 101 which includes the light source(s) 120, the scanner 130, projection optics 140 and optionally and preferably eye tracking system 160. Optionally, other components, including a power source such as battery (not shown) may optionally be located in a remote module 102 which can also be portable but need not be located in proximity to the eye 155. However, at least the power source of remote module 102 is connected to head-mounted part 101 with a wire 103 or other power connector or cable.

Figure 2:
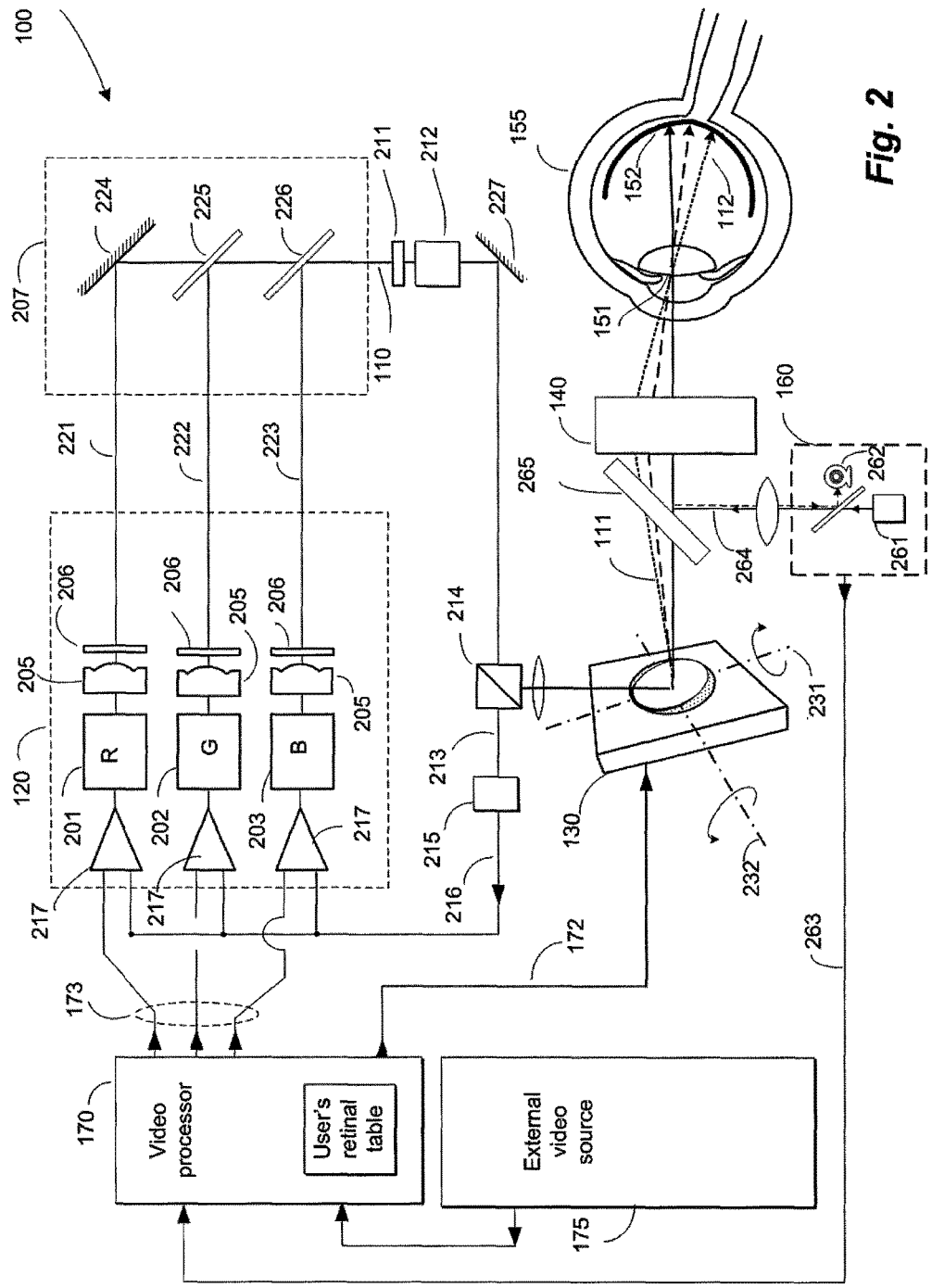
FIG. 2 describes various illustrative non-limiting embodiments of the present invention, the VRD 100 comprises light source(s) 120 such as for example a laser, or more particularly a laser diode.

Turning now to FIG. 2, which describes various illustrative non-limiting embodiments of the present invention, the VRD 100 comprises light source(s) 120 such as for example a laser, or more particularly a laser diode. The VRD 100 may contain one or several light sources 120. Particularly, if the raster scanned image that is projected onto retina 152 is to feature colors, which may be represented by RGB (red, green, blue), light sources 120 preferably feature at least three lasers which emit at red, green and blue (designated 201, 202, and 203 respectively). Although lasers are convenient light sources due to their brightness and low beam divergence, the light sources 120 do not need to be coherent or at a narrow spectral width; light emitting diodes (LED) may also optionally be employed.

The individual light sources 120 are preferably further provided with collimation optics 205 as shown. Preferably the light beam 110 emitted has low divergence. Light emitted from a laser source can become collimated to a beam with a very small divergence angle. However, collimation of incoherent light as LED is more difficult. The LED can be collimated by using an aspheric lens with numerical aperture greater than or equal to numerical aperture of the beam, which could for example optionally be incorporated into collimation optics 205 as shown. However due to the finite size of the source, the beam will have residual divergence. Nevertheless, since VRD 100 comprises further optical elements to project the light into the pupil 151, such as projection optics 140 for example, a LED source can still provide sufficient intensity and low divergence to be utilized as light source 120.

The light sources 120 are optionally and preferably further provided with a light attenuator 206 such that the light emitted from light source 120 is well within the eye-safe intensity level.

Light attenuator 206 may optionally comprise silica glass or ceramics for example. When several light sources 120 are used, such as for example to provide projection of color images, each light source 120 is optionally and preferably provided with a separate light attenuator 206, as shown in the exemplary configuration of FIG. 2.

Projection of color images provides a particular challenge, because the intensity perception of the eye 155 is different at each color (wavelength); therefore each color needs to be attenuated separately and to a differing degree to comply with eye-safety requirements at the specific spectral range. The required safety levels are typically given in various regulations and directives e.g., the US standard ANSI Z136 or the European standard EN 207.

When VRD 100 comprises RGB light sources 120 as shown, the beams from individual light sources are optionally and preferably combined by a beam combiner 207 based on dichroic filters, or spectrally dispersive components, to form light beam 110. In an exemplary arrangement shown in FIG. 2 the beam of red light 221 emitted from the red light source 201 is first bent by mirror 224 and subsequently combined with beam of green light 222 by dichroic filter 225. The dichroic filter 225 transmits the red light 221 and reflects the green light 222. Similarly, dichroic filter 226 reflects the blue light 223, while the red and the green beams 221, 222 are transmitted. As a result a beam of light 110 that contains all RGB components is emitted from the beam combiner 207.

Optionally, an additional light attenuator 211 is situated to receive light beam 110. Optionally the light passes a polarization control unit 212 that can contain polarizers, waveplates such as λ/2 or λ/4, or other optical elements for controlling the polarization. In one or more embodiment additional attenuation can be provided by the polarization elements of polarization control unit 212. For example and without limitation, a non-limiting example of a device that could be used to implement polarization control unit 212 is a variable attenuator based on polarization control, which may for example and without limitation be purchased from Newport Inc. (Irvine, Calif., USA), (http://assets.newport-.com/webDocuments-EN/images/Variable Attenuators.pdf).

In some optional, exemplary arrangements, in order for greater efficiency in the spatial placement of different elements the beam 110 can be further deflected, here shown as being bent by mirror 227.

Optionally and preferably part of the light beam 110 then passes through an intensity monitor unit ("light tap") 215. A small fraction of light 213 is split from the beam 110 by a beam splitter 214, typically 1% to 5% of the main beam 110. Light fraction 213 is then fed to intensity monitor unit 215 and used to monitor the light intensity. In preferred embodiments the signal from intensity monitor 215 is used as a feedback signal 216 to control the light intensity and to disable (shut off) the light sources 120, which provides additional level of safety to the operation of VRD 100.

For example as a non-limiting illustration of the operation of light intensity control for safety, feedback signal 216 is optionally and preferably communicated to control logic electronics 217 (shown for one light source 120 but which could optionally control all light sources 120; alternatively each light source 120 could have its own control logic electronics 217). Control logic electronics 217 compare the value of the power of light source 120, such as a laser for example, to a predetermined value (which corresponds to eye-safe power value). If the monitored light power is exceeds the predetermined value, then control logic electronics 217 would shut down the respective light source 120 or light sources 120. The light source 120 can be disabled in a variety of ways, for example by interrupting the supply of power to light source 120 by a switch(not shown) If the light source 120 is a laser diode then control logic 217 is preferably implemented in the driver wherein light emission is disabled by turning off the current to the laser. Control logic electronics 217 is an example of a modulator, albeit in the form of a cut-off device. However, light beam 110 is also optionally intensity modulated as follows. The video processor 170 generates a modulation signal 173 according which the beam of light 110 is intensity modulated. Generally there are two methods to modulate the intensity of the light beam 110. In direct modulation the intensity modulation is achieved by modulating the current driving the light source 120, which may for example be a laser diode. When the light source 120 is directly modulated the emitted beam of light 110 emerges from the source 120 already intensity modulated. When an external modulation is utilized such as for example acousto-optic modulator, the modulation signal 173 is fed as a drive signal to a transducer of the acousto-optic modulator.

In arrangements where more than one light source 120 is used, as for RGB light sources, the modulation signal is preferably provided to all sources 120, according to the RGB video information for RGB light sources. When external modulation is used, the signals are communicated to the external modulator drivers and each light source 120 is provided with a modulator (not shown). As mentioned above the VRD 100 may include a safety feature where the laser is disabled by the intensity monitor signal 216. Those skilled in the art will appreciate that other types of modulators can be utilized.

The dynamic range of the modulation is defined by the original image data requirements and it is limited by the actual modulation ability of the chosen light modulating device. Regardless of the configuration, the light beam 110 incident on the scanner 130 is intensity modulated. With color projection each individual beam is intensity modulated according the RGB video information before being combined to light beam 110.

The beam scanner 130 is used to steer or deflect the light beam 110 horizontally and vertically in a two dimensional raster pattern. The deflected beam 111 is further focused on the retina 152 by the projection optics 140, and optical system of the eye 155. A particular point on the retina 152 where the light focuses (such a point may also be referred to herein as a "pixel") corresponds to a particular horizontal and vertical angle spanned by the scanner 130. The focused beam 112 scans the retina 152 as the scanner 130 causes focused beam to scan horizontally and vertically. The intensity of the focused beam corresponds to the light intensity of the modulated beam 110. In such a manner a raster display is drawn directly onto the retina 152 which the user perceives as an image.

According to at least some embodiments, beam scanner 130 features a fast steering mirror for creation of the row raster, described herein as horizontal scanner 231, and a slow addressable axis spanning the rows, described herein as vertical scanner 232. MEMS (micro-electro-mechanical systems) scanners such as for example available from MicroVision (www.microvision.com), are usually biaxial and so may optionally be used to implement both horizontal scanner 231 and vertical scanner 232, such that the slow and fast scanners are optionally incorporated in a single such device.

Scanner requirements for horizontal scanner 231 and vertical scanner 232 are defined by at least the following factors: frame rate, resolution, pixel count, and optical system limitations. Fast steering axis ("horizontal scanner") 231 frequency is defined as [M of rows in a frame]×[N of frames], in which each frame is an image projected onto the retina as the previously described raster display which is composed of a number of rows M. Slow steering axis ("vertical scanner") 232 movement bandwidth is determined by the required frame rate. It is preferable to use an addressable scanner with position feedback for this purpose in order to be able to compensate for various aberrations of the surfaces of the optical path, including with regard to any aberrations of the various lenses and mirrors in the optical path.

Each of horizontal scanner 231 and vertical scanner 232 is preferably driven by video processor 170 according to synchronization signal 172 for the scanning voltage, but may also include a slow varying voltage that depends on the feedback signal 263 received from the eye tracking system 160 as will be explained further.

Another optional mode of projection is vector scan where the light is steered between specified points, which may also be implemented according to various embodiments of the present invention. The mirrors (that is, horizontal scanner 231 and vertical scanner 232) do not span the entire field of view but move along a specified path. Vector scan mode requires addressable scanners that operate in a close loop with feedback on their position and velocity for both axes.

Turning back to the implementation shown in FIG. 2, the projection optics 140 acts in conjugation with the refractive optical system of the eye 155 to convey the light beam through the pupil 151 and focus on the retina 152. The projection optics 140 is designed such that the beam of light 111 deflected by the scanner 130 at angles spanning the entire field of view (FOV) essentially crosses the optical axis at the center of pupil 151 while avoiding vignetting. Vignetting is a visual artifact which occurs when the peripheral parts of an image appear darker, due to a reduction of the image's brightness or saturation at the periphery compared to the image center.

Figure 3:
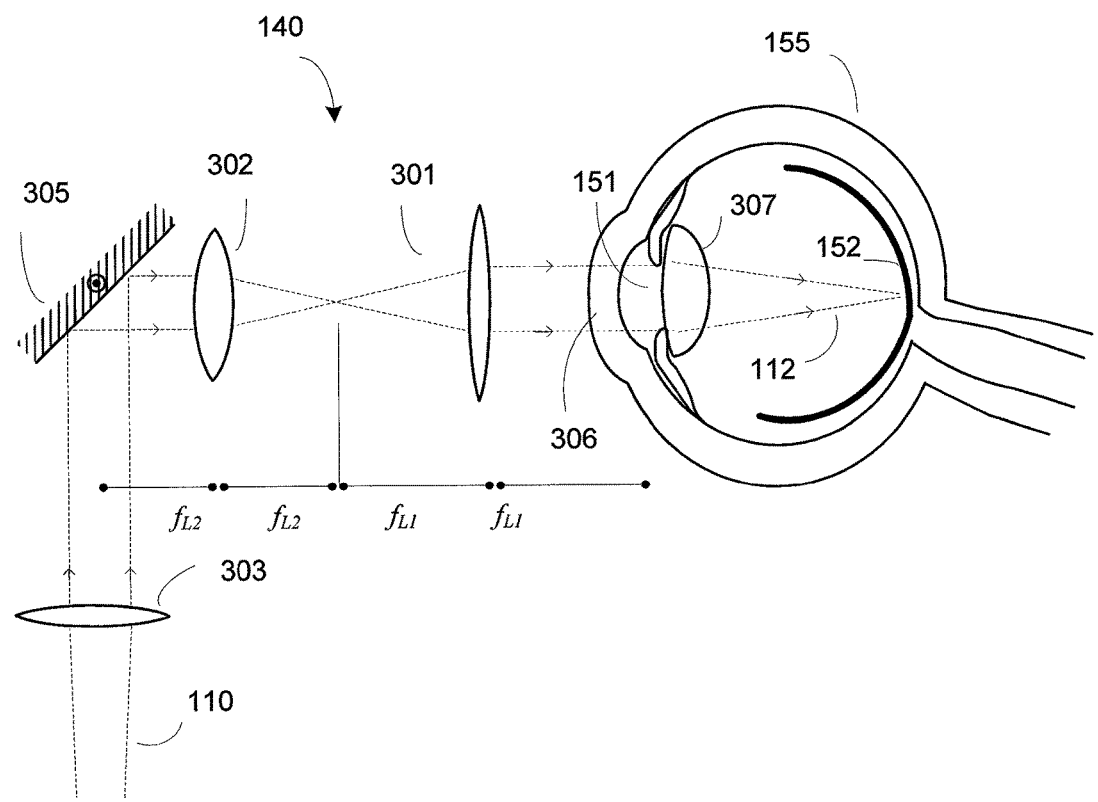
FIG. 3 shows an exemplary, illustrative, optional embodiment of the projection optics 140 as a schematic block diagram.

FIG. 3 shows an exemplary, illustrative, optional embodiment of the projection optics 140 as a schematic block diagram, in which some components have been omitted for the sake of clarity. The specific embodiment shown features an arrangement sometimes referred to as a "4-f scanner design" where the scan mirror 305 is conjugated with the pupil 151. Lens 301 is positioned essentially such that its back focal plane coincides with the pupil 151. Focusing of the beam 112 on the retina 152 is achieved by the refractive mechanism of the ophthalmic system of eye 155, particularly the cornea 306 and the lens 307. The front focal plane of lens 301 coincides with back focal plane of lens 302. If the scan mirror 305 is positioned at the front focal plane of the lens 302, then essentially the pupil 151 is always filled completely at all positions of scan mirror 305, since the scan mirror and the pupil are optically conjugated. A third lens 303 may be required so as to provide the fine tuning divergence of the collimated beam 110.

Other designs of projecting optics for projections optics 140 are optionally possible including but not limited to more optical elements depending on details of the optical components such as light sources and scanner, and to account for refraction errors of the ophthalmic system (e.g., astigmatisms; not shown). Optionally, an additional lens (not shown) is provided to overcome for ophthalmic conditions such as myopia, or hyperopia, hence a certain beam divergence, or convergence, need to be introduced, while on the other hand a perfectly collimated beam is preferably adapted for individuals that require no refracting correction.

The projection optics 140 can be designed such that no light other than projected light beam 112 passes to the user's eye 155, or alternatively the projection optics 140 can be designed such that the user views the real world separately from the projected image. When the projection optics 140 is designed so that the user also views his/her surroundings in addition to the projected image, the virtual image projected by the VRD 100 is preferably superimposed on the image of the real-world.

Figure 4:
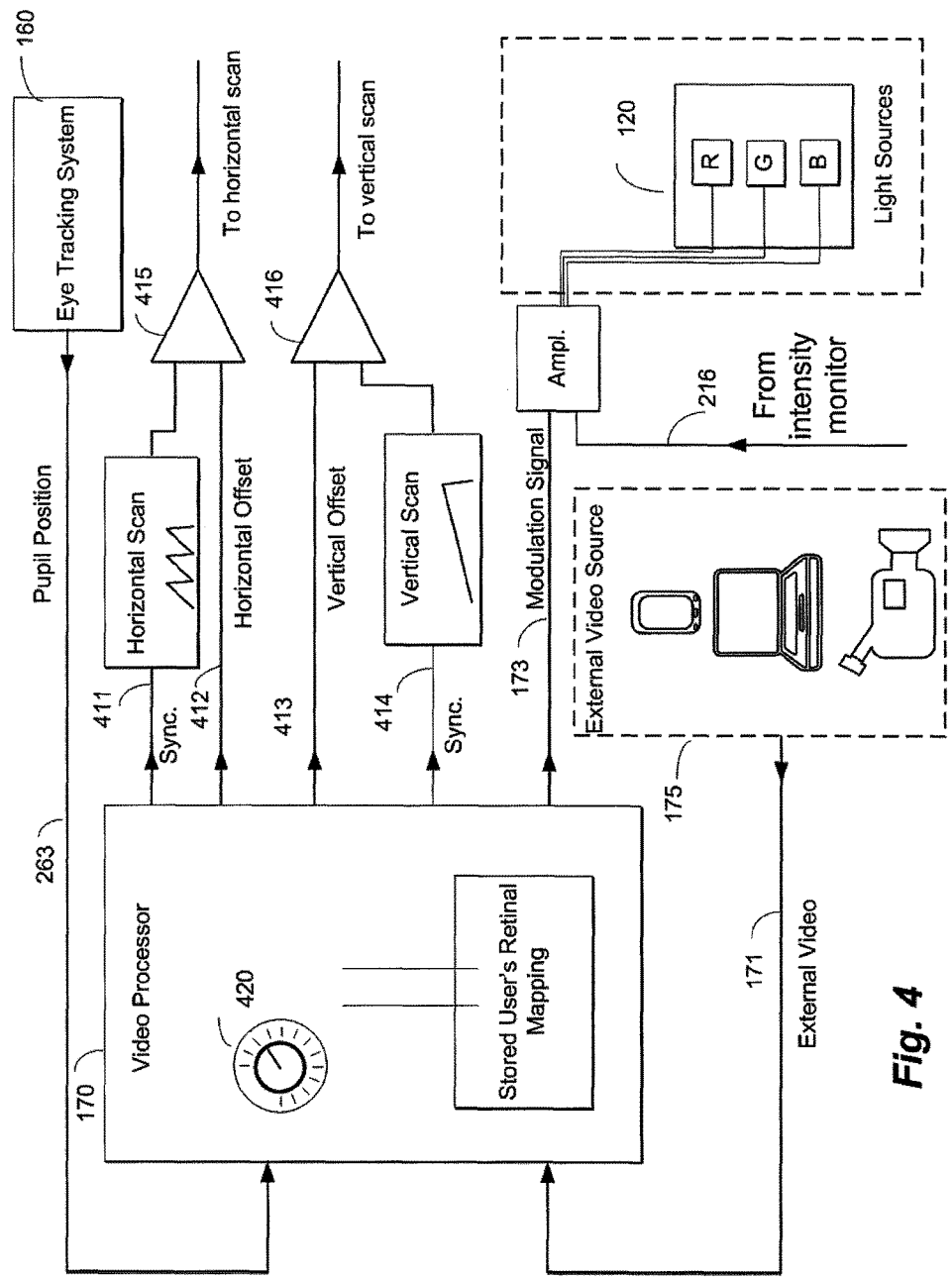
FIG. 4 shows operation of video processor 170.

Returning back to FIG. 2, the VRD 100 optionally and preferably further comprises an eye tracking system 160 that may contain an IR illumination 261 and IR sensitive camera 262 which captures IR reflections from the outer surface of eye 155 and in this way detects the position of the pupil 151 as it moves. The IR light path 264 can be combined with the video signal light by a beam combiner 265. The instantaneous position of the pupil 151 provides a feedback signal to offset the scanner 130 deflection in the direction of the pupil 151, and is further processed in the video processor 170 to derive the video information to be projected onto retina 152. The operation of video processor 170 will now be explained also in conjunction with FIG. 4.

The video processor 170 optionally and preferably receives two main external input signals: an external video signal 171 from an external video source 175, namely an electronic device which generates video data such as a camera, a computer display, a mobile device or any other device that can generate video data (not shown). A second input to the video processor 170 is preferably a signal communicated by the eye tracking system 160 of the instantaneous position of the pupil 151. Other inputs to the video processor 170 not shown for clarity may optionally include feedback from the scanner and the instantaneous intensity communicated by intensity monitor unit 215.

The video processor 170 preferably has two main output signals: it provides the signal of modulation of light beam intensity (modulation signal 173), and provides signal 172 to the scanner 130 synchronized with the modulation signal 173.

The signal 172 to the scanner 130 is composed of total of four signals, two for each scanning axes. The signal to each scanning direction is composed of high frequency signal that triggers the raster scan, and a slow varying voltage which is an offset to the scanning mirror 130 to track the instantaneous position of the pupil 151.

In a light tracking system light, typically infrared, is reflected from the eye 155 and sensed by a video camera or some other optical sensor 262. The information is then analyzed and the position of the pupil 151 is determined. In response to the detected position of the pupil 151, the scanning mirror 130 is moved, both vertically and horizontally, such that the exit pupil of the VRD 100 is aligned with the pupil 151.

Accordingly, the video processor 170 generates a high frequency signal 411 for triggering the raster scan in a horizontal direction, and slow varying signal 412 for horizontal offset which are fed through an amplifier stage 415 to horizontal scan 231 of the scanning mirror 130. Similarly, the video processor generates a high frequency signal 413 for triggering the raster scan in a vertical direction, and slow varying signal 414 for vertical offset which are fed through an amplifier stage 416 to vertical scan 232 of the scanning mirror 130.

The input of the pupil position also serves to process the projected video frame from the external video frame as follows. The entire retinal field of view (FOV) is decided by the largest angle of light rays that enter the pupil and reach the retina. Rays projected at higher angles will not reach the retina and hence will not be perceived. The virtual image projected by the VRD can be tuned to match exactly the frame size of the incoming external video, or alternatively the VRD can be tuned to project only part of the external video frames. When the external video signal that enters the video processor fills the entire retinal FOV the virtual retinal image is said to be at unity magnification (×1). When the VRD projects only part of the external video frame across the entire FOV of the retina the VRD operates at larger magnifications. It should be noted that "magnification" in this example refers to the portion of the external video frame that is projected onto the retina, such that such a frame can be said to be magnified when only part of the frame is projected over the retinal FOV. It should also be noted that the retinal FOV does not necessarily refer to the entire retina, as described in greater detail below, since part of the retina may be damaged or inoperative.

Operating at high magnification can be useful when the incoming video corresponds with panoramic scenes. The situation is similar to an ordinary process of visual perception when an extended (panoramic) object is viewed. The user moves her pupil across the object in such a manner that different parts of the object are perceived at a given position of the pupil. The instantaneous position of the pupil therefore defines a partial frame of the object that the user perceives. When the VRD operates at magnification higher than unity the instantaneous position of the pupil defines the part of the external video frame that can be projected to the retina. The video processor stores the external video frames in a buffer, and according the instantaneous position of the pupil, processes a sub-frame to be projected by the VRD to accommodate available FOV. The central part of the frame corresponds to the center of the pupil where the pupil aperture defines the "window" frame.

Operating the VRD at large magnification can be particularly advantageous when used by individuals with impaired vision as a visual aid where magnification can be beneficial. For example, when certain regions in the retina are damaged, as in age related macular degeneracy (AMD), the parts of the image that fall on those parts are not perceived. When the image is magnified details of the magnified image are projected over the undamaged parts in the retina which can compensate for the damaged ones. The shortcoming in magnification is that peripheral parts of the external video frame are not imaged.

The VRD of the present invention, according to at least some embodiments, is provided with tunable magnification controller 420 that can be adjusted by the user to provide input to video processor 170 regarding the extent of desired magnification. When higher magnification is required, such as for example when reading textual graphics the user adjusts the magnification such as the text is readable; when wider panoramic view is desirable the magnification can is adjusted to unity, that is, to correspond to the original (external) video.

The frame processed from the external incoming video is further processed in the video processor with respect to retinal mapping of each individual as explained below.

A retinal sensitivity map, or map of levels of retinal function at different locations (pixels), is preferably provided for the best operation of the below described method according to at least some embodiments of the present invention. Art known devices failed to include such a map, which means that they would not be effective for individuals having damaged retinas or retinas with reduced and/or uneven functioning. The map is preferably obtained by a mapping unit, which may optionally and preferably be implemented with the device of FIGS. 1 and 2 according to at least some embodiments of the present invention. All of the functionality of the mapping unit may optionally be implemented with the projection unit (shown as the apparatus of FIG. 2 above in a non-limiting example), including the mapping software and analysis functions; alternatively these latter functions may optionally be performed separately and then the results fed to the processing unit of the projection apparatus. It may optionally be performed offline by a separate computer or alternatively through a combined device.

Electroretinogram (ERG), pattern ERG (PERG), visual evoked potential (VEP) and other optometric and ophthalmic tests described in the art specify the visual field of an individual wherein these test provide information of an loss of vision or a reduction in sensitivity (threshold) of selected areas of the human retina. These tests are well known in the art and may optionally be implemented with various types of apparatus, also as known in the art. For example, U.S. Pat. No. 5,233,373 describes an apparatus and a method of use thereof for implementing a PERG test on a retina of a patient, which is hereby incorporated by reference as if fully set forth herein, which includes a method of testing different locations of the retina in order to determine the relative level of function of these locations.

Figure 5:
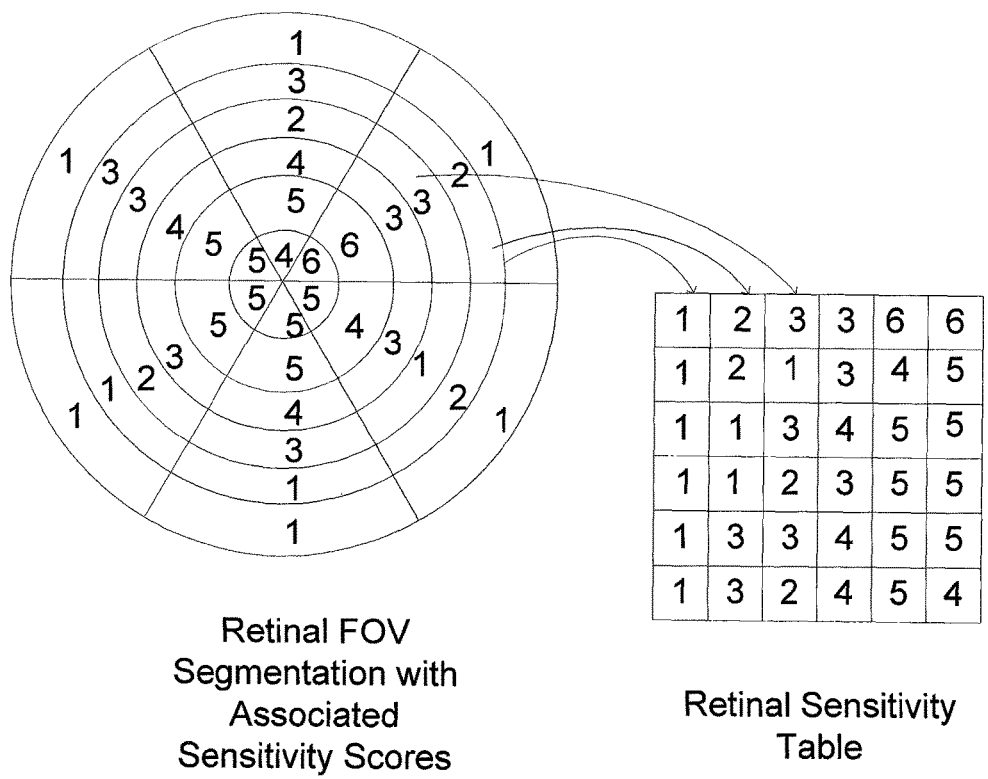
FIG. 5 is an exemplary segmentation of retinal FOV where each angular segment is represented with a cell in the RST.

The sensitivity (to different levels of light) and resolution of the diagnostic test (i.e.,—the pixel density) and of course the retinal function of the subject will all determine the retinal map that is obtained. According to at least some embodiments of the present invention, the retinal sensitivity map obtained in ophthalmic evaluation is decoded into a retinal sensitivity table (RST). A typical adult human retina is about 72% of a sphere of 22 mm in diameter. The entire retinal field of view (FOV) is decided by the largest angle of light rays that enter the pupil and reach the retina. Shown in FIG. 5 is an exemplary segmentation of retinal FOV where each angular segment is represented with a cell in the RST; the row number and column number corresponds to an angular sector of the entire retinal field of view area element, and the value in the cell represents the sensitivity of the area as follows: the highest level of sensitivity has the score 1, the second level of sensitivity has the score 2, and so forth, where complete loss of vision is represented with the highest number.

The sensitivity scale is decided by the resolving capability of the applied diagnostic test; optionally also the number and location of the cells are determined according to the capabilities of the applied diagnostic test.

According to at least some embodiments of the present invention, the retinal map is transformed into the RST according to one or more conversion factors; for example, if the resolution of the diagnostic test is lower than expected for conversion to the RST, then the conversion process needs to accommodate this lowered resolution in order for all cells of the RST to be populated with data. The placement of the eye, and specifically of the pupil, during the diagnostic test from which the retinal map is obtained also needs to be considered with regard to the transformation to the RST, so that any movements of the pupil away from the placement during the test may be suitably compensated. Preferably, the diagnostic test is applied more than once, so that the retinal map is obtained a plurality of times with the pupil in a plurality of different locations, in order to assist with the transformation process and also with calibration of the RST according to pupil movements.

As the light signal is scanned in horizontal and vertical directions and projected onto the user eye the light signal is scanned over the user retina, horizontally and vertically. Since the RST represents a map of the retina where each cell corresponds to a retinal sector or pixel, it is important that the RST is arranged according to the light scan trajectory.

RST represents the absolute sensitivity of different sectors of the retina, which is non-uniform (non-homogenous) even for a normal retina, i.e., of a healthy individual with unimpaired vision. Certain portions of the retina are more sensitive to the light than other portions even in such an individual. For individuals with diseased or damaged retinas, the lack of uniformity may be much more pronounced, even to the point of having non-functioning parts of the retina. A relative RST (RRST) is constructed, where sensitivity values or the RST obtained for an individual are normalized relative to standard RST, obtained for individuals with normal vision. Such a standard RST may optionally be obtained for a particular population or alternatively is obtained for a number of individuals with healthy, normal vision, and is then used for calibration of RSTs obtained from individuals that are to receive the retinal projector apparatus as described herein.

For clarity, by way of example, in what follows the relative sensitivity scale will be of 16 levels, with 16 being the score of complete loss of vision. FIG. 6 is an example of the first 10 rows by 10 columns of an illustrative RRST, for a retina which demonstrates reduced sensitivity within the center of this region, such that sectors corresponding to row 6, column 5, and row 6 column 6 (written as (6,5) and (6,6) for short) correspond to lower functionality and hence greater loss of vision, while the peripheral pixels of this region still have normal sensitivity as compared to healthy individuals.

Figure 7:
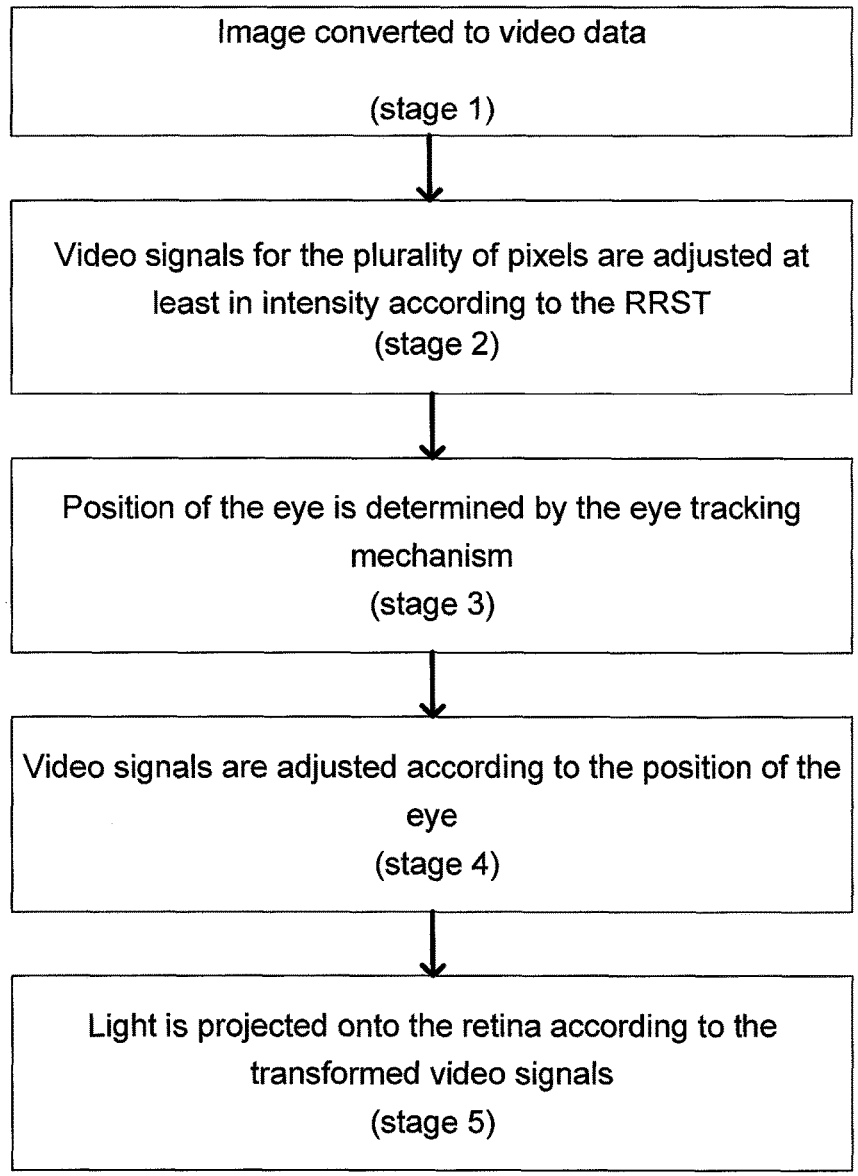
FIG. 7 relates to an exemplary, illustrative method for receiving an incoming image and for projecting that image appropriately onto the retina of the subject through the retinal projection apparatus.

FIG. 7 relates to an exemplary, illustrative method for receiving an incoming image and for projecting that image appropriately onto the retina of the subject through the retinal projection apparatus, for example as described herein. The method may be generalized for a plurality of images by repeating the process described herein for one image.

As shown, in stage 1, the external digital image is converted to respective video signals for a plurality of pixels.

In stage 2, these video signals for the plurality of pixels are adjusted at least in intensity according to the RRST, to form transformed video signals. According to at least some embodiments, the method is adjusted if there are some parts of the retina that are so damaged or reduced in function that they are practically inoperative, at least in terms of receiving projected light, as described in greater detail below with regard to FIG. 10. For this non-limiting example and embodiments, all (or nearly all) of the pixels of the retina receive projected light.

As will be explained below one purpose of the RRST is to generate selective augmentation of light signals from the Retinal Scanner for those retinal segments with impaired sensitivity. For reason of simplicity the explanation we will assume a single color, but it is understood that similar is applicable for multi-color, (typically red, green and blue (RGB) video signals.

Figure 8:
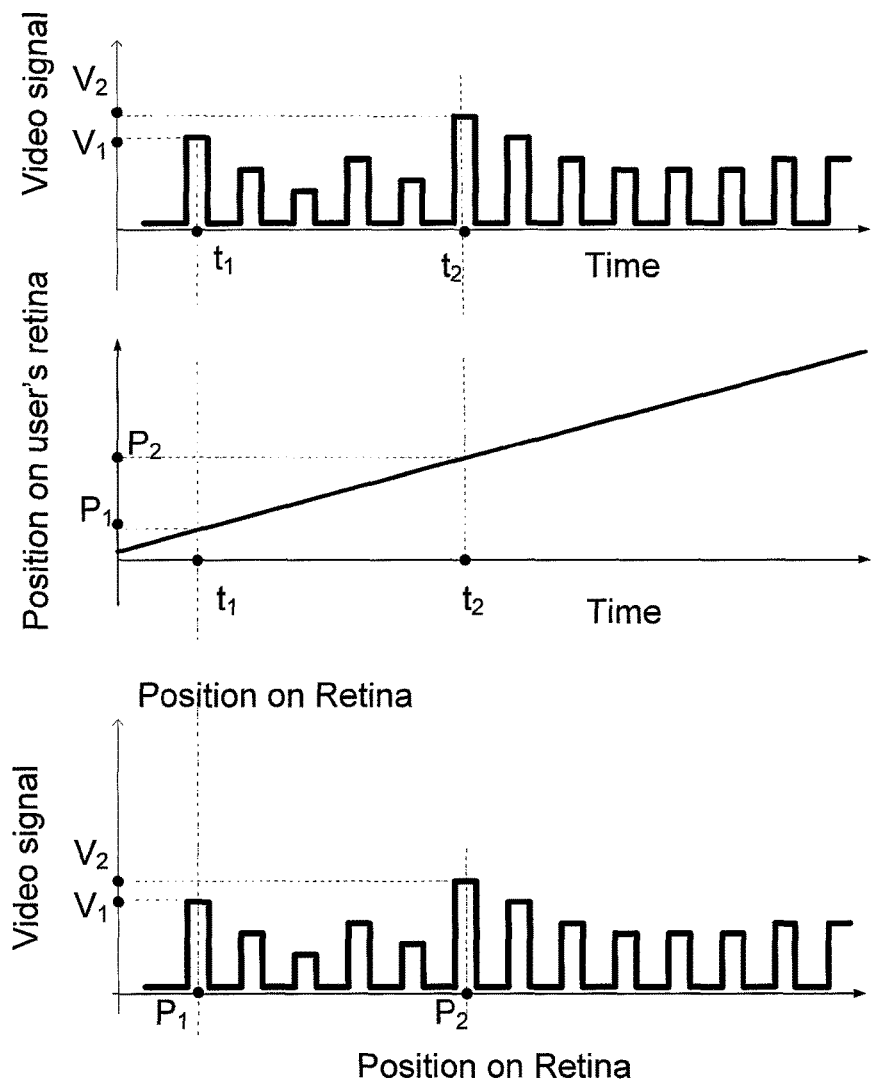
FIG. 8 (upper plot) shows exemplary analog video signal derived from the camera of a raster scan; the middle plot shows the retinal position of the light signal during the scan; the lower plot shows the video signal along the retinal position.

The upper plot in FIG. 8 shows exemplary analog video signal derived from the camera of a raster scan; the middle plot shows the retinal position of the light signal during the scan. At time $t_1$ the video signal corresponds to the value $V_1$, at the same time the retinal position is $P_1$. At a time $t_2$ the video signal has the value $V_2$, while the retinal position at that instance is $P_2$. The lower plot shows the video signal along the retinal position.

Figure 9:
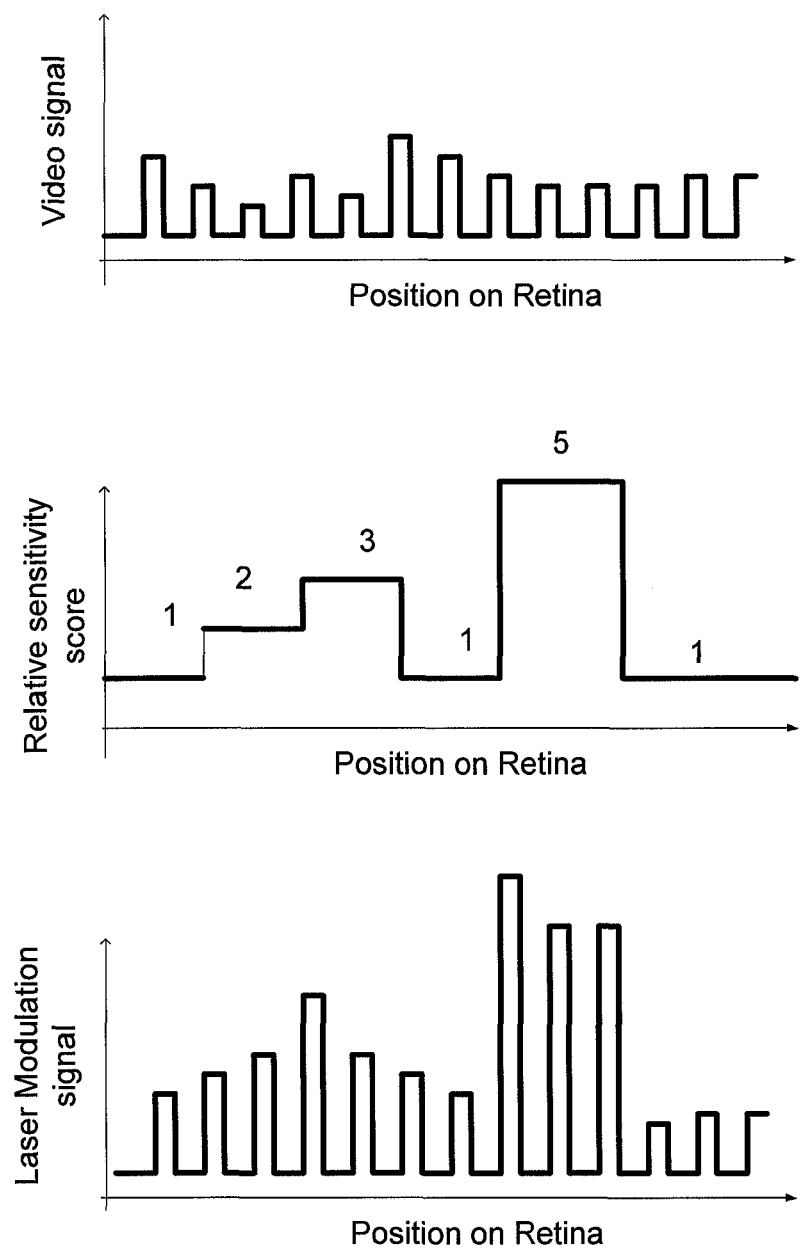
FIG. 9 (upper plot) is a video signal resulting from the camera, here shown as a digital signal for clarity; the middle plot indicates the relative sensitivity scores of the retina according the position of the retina.

According the present invention as the light source is modulated with the respective video signal, the modulation depth is set by the RRST. This is best demonstrated in FIG. 9. The upper plot is a video signal resulting from the camera, here shown as a digital signal for clarity. The middle plot indicates the relative sensitivity scores of the retina according the position of the retina. The light source (a laser, LED or other light source) is modulated with signal which is the multiplication of video data (signals) from the camera with the value of the RRST given and corresponding to the video data.

The function of the RRST can be also understood as follows. In the process of unaided vision the user creates the image of the observed scene on the retina. To every point in the observed scene (object) corresponds a small area element on the retina. In one embodiment of the present invention an image is acquired by a digital camera. Every pixel in the camera image corresponds to particular point in observed object. Therefore every pixel in the camera image is associated with an area element in the user retina. To compensate for impaired sensitivity in certain area elements of the retina, the camera image is intensified in those pixels associated with the retinal elements with a reduced sensitivity. The RRST contains the information where the image should be intensified, and the amplification factor. Mathematically, if the image of the camera is represented by a matrix M, the RRST is represented by the matrix R, then the intensity corrected matrix A results in $$A_{i,j} = R_{i,j} M_{i,j}$$

where each element (i,j) in A is multiplication of the associated element (i,j) of the original image matrix M, and the associated element (i,j) in RRST R.

Retuning again to FIG. 4 the video processor before conveying the signal to intensity modulator preferably processes the projected video frames by multiplication with the RRST as explained. It should be noted that when the user moves his pupil to observe different region of the object he moves his eyeballs, and therefore the retina is shifted accordingly. In this sense the RRST is determined according to the relative position of the user pupil. When the VRD operates at magnification larger than ×1 only a portion is available to the user at a specific location of the pupil. The user moves his pupil to observe the entire panoramic view. Since the RRST is affixed to the pupil the mapping of RRST needs to be processed only on the projected image which is smaller than the buffered image external video image.

In stage 3, the position of the eye, and hence the relative location and angle of the pupil is determined by the eye tracking mechanism. In stage 4, the video signals are adjusted according to the position of the eye: more specifically, the eye tracker provides the feedback to offset to the scanners mirrors so that the exit pupil of the Retinal Display (i.e.—the light projector) is approximately aligned with the entrance pupil of the eye. The instantaneous position of the pupil is also feedback to the video processor, such that only the video signal associated to the visible window as determined by the instantaneous position of the pupil is transferred to logic unit and multiplied according to the RRST and its associated sync signals are fed to the scanner mirrors. In stage 5, light is projected onto the retina according to the transformed video signals.

Stages 3-5 are optionally and preferably repeated for each row or column of pixels for the transformed video signals, as necessary in order to project the entire image onto the retina.

According to at least some embodiments of the present invention, there is provided an exemplary, illustrative method for projecting light onto a retina in which at least a portion of the retina is effectively non-functional. By "effectively non-functional" it is meant that the specific portion of the retina cannot respond with sufficient functionality to be able to effectively receive projected light. Such effectively non-functional areas may include for example scotomas.

Figure 10:
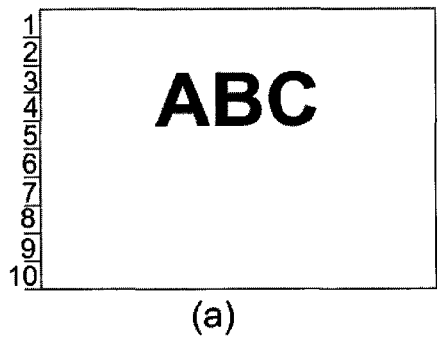
FIG. 10, in the upper diagram (10a), shows an image of letters ABC represented with the retinal projector as raster scan of row 3 and 4; the second diagram of FIG. 10 (10b) represents how the projected image appears in field of vision with stocoma at the central portion; the third diagram of FIG. 10 (10c) shows the letters ABC when the raster image was projected at rows 5 to 6.
Figure 10:
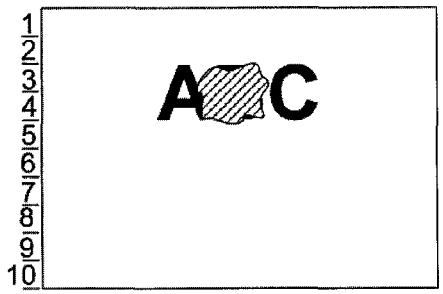
Figure 10:
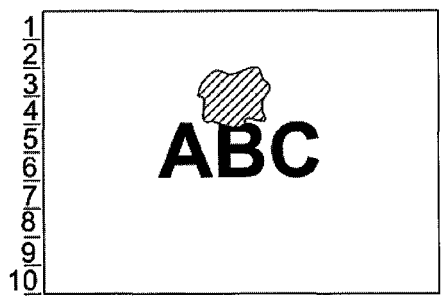
Figure 10:
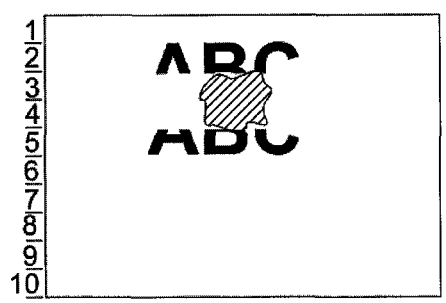

When the field of vision contains scotomas where the visual acuity is entirely degenerated, it may be advantageous to shift the image off the degenerated sectors towards healthy sectors of the retina. This is particularly true when the scotomas appear in the central field of vision. Referring to FIG. 10, in the upper diagram (10*a*), shows an image of letters ABC represented with the retinal projector as raster scan of row 3 and 4. The second diagram of FIG. 10 (10*b*) represents how the projected image appears in field of vision with stocoma at the central portion. The third diagram of FIG. 10 (10*c*) shows the letters ABC when the raster image was projected at rows 5 to 6.

The degree of severity of stocoma and its position within the retina is deduced in the RRST. If the region where significant part of field of vision is degenerated to the extent of complete vision loss then according to the present invention the respective video information is translated to the raster scanned rows corresponding to healthy sectors.

The circumvention of degenerated sector in the retina can be in non-continuous signals such that the projected image has certain "black" rows corresponding to rows where light is not projected.

The projected image can appear as in the last graph (10d) of FIG. 10 in which the image was broken and re-projected at rows ahead.

Figure 11:
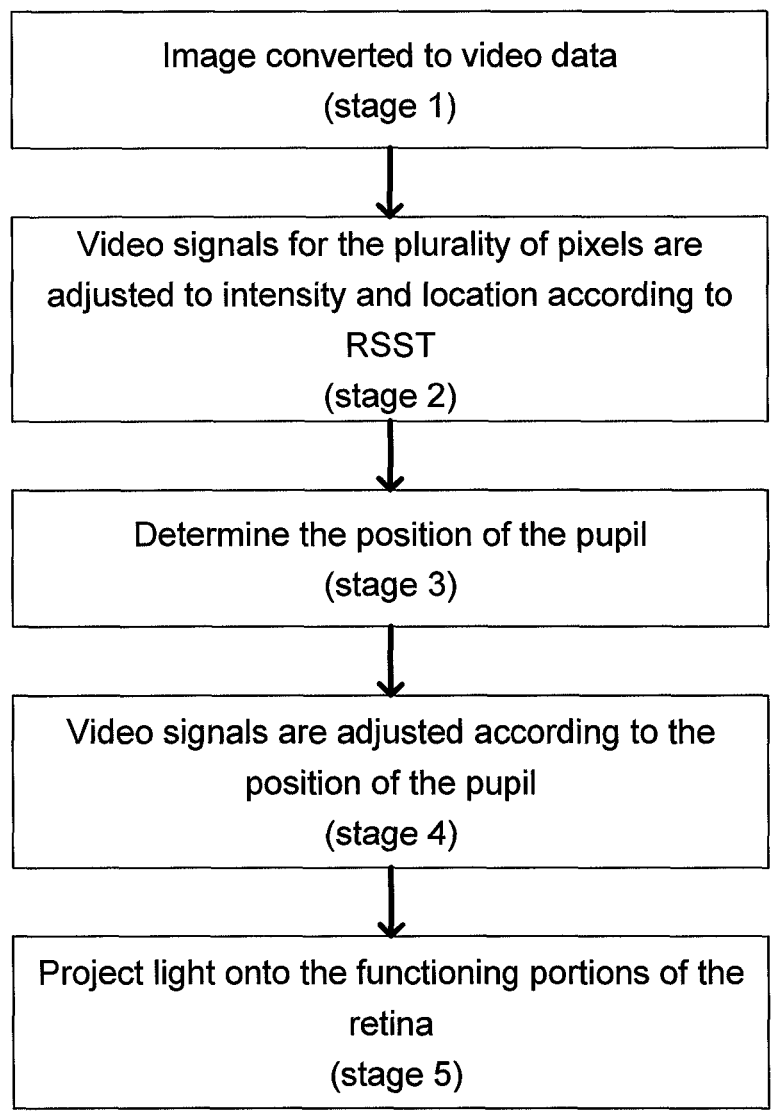
FIG. 11 relates to an exemplary, illustrative method according to at least some embodiments of the present invention for receiving an incoming image and for projecting that image appropriately onto the retina of the subject through the retinal projection apparatus, for example as described herein, in which one or more portions of the retina are essentially non-functional.

More specifically, this method may optionally be performed as follows. FIG. 11 relates to an exemplary, illustrative method according to at least some embodiments of the present invention for receiving an incoming image and for projecting that image appropriately onto the retina of the subject through the retinal projection apparatus, for example as described herein, in which one or more portions of the retina are essentially non-functional. As for FIG. 11, the method may be generalized for a plurality of images by repeating the process described herein for one image.

As shown, stage 1 may optionally be performed as for FIG. 7.

In stage 2, due to one or more essentially non-functioning parts of the retina, at least a portion of these video signals for the plurality of pixels are adjusted both in intensity and also in location according to the RRST, to form transformed video signals. At least some video signals may optionally be adjusted only in intensity, but for the sake of clarity, the description herein focusses on those signals which need to be adjusted both in intensity and location.

In stage 3, the position of the eye, and hence the relative location and angle of the pupil according to a previously determined position during the previously described diagnostic test, is determined. In stage 4, the transformed video signals are adjusted according to the position of the eye and more specifically, any differences between the current location and angle of the pupil, and the previously determined location and angle of the pupil during diagnostic tests. For example, depending upon movement of the pupil a "high" signal at a pixel may in fact be transformed to a "low" signal to be projected at a pixel, effectively shifting and transforming the map according to the current pupil position, but may also determine whether a signal is sent at all, as described in greater detail below.

Figure 12:
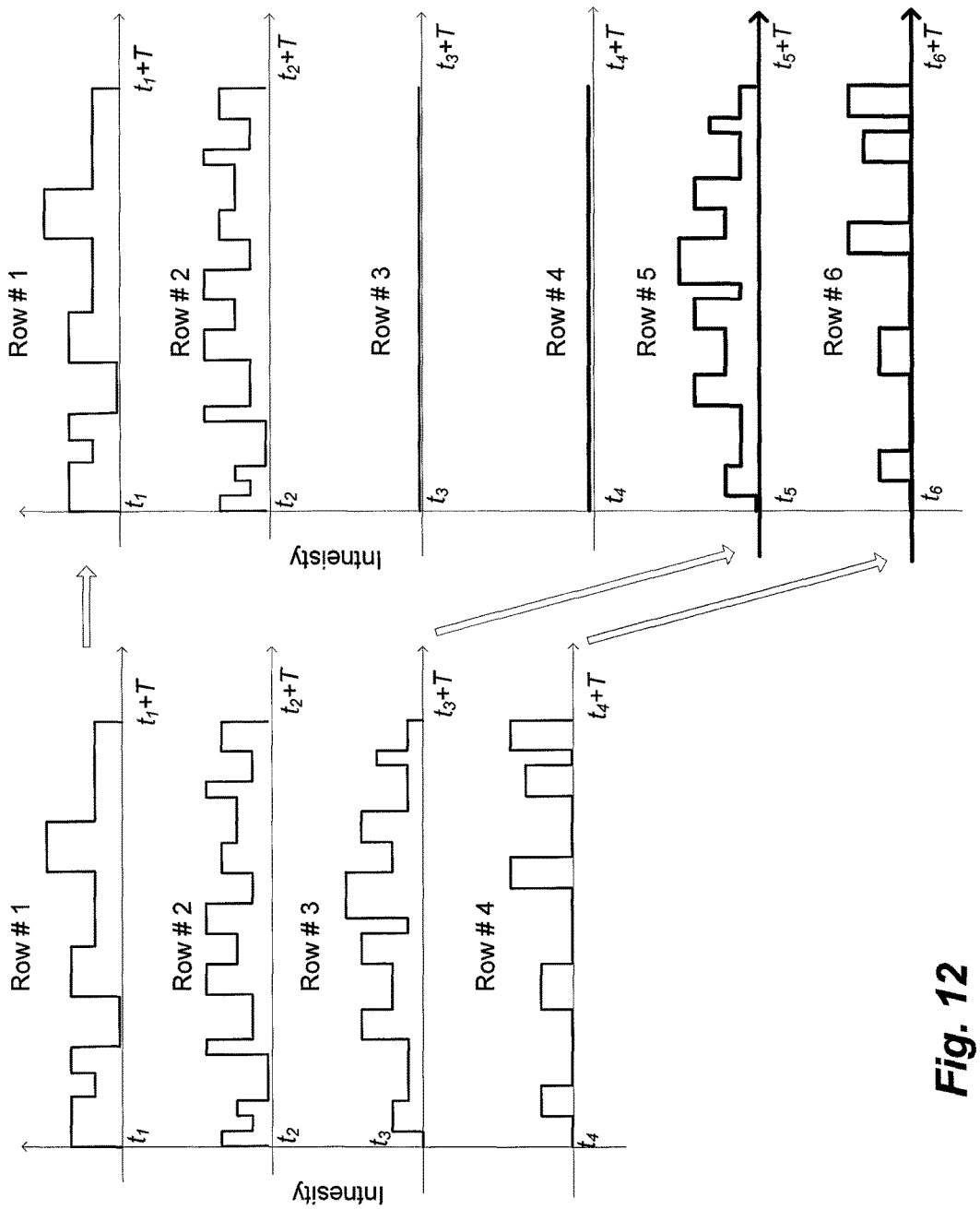
FIG. 12 shows the schematics of an exemplary, illustrative scan over the field of vision where the indicated path, in the shape of an "S-curve" with a plurality of inflection points, indicates the trajectory of the scan.

According to at least some embodiments of the present invention, adjusting the location of the video signals is performed as follows. Translating a portion of the image from degenerated to healthy portion of the retina is accomplished by introducing a controlled delay of the video signal relative to the raster scanner. FIG. 12 shows the schematics of an exemplary, illustrative scan over the field of vision where the indicated path, in the shape of an "S-curve" with a plurality of inflection points, indicates the trajectory of the scan. The frame starts at time indicated by t0. With a bi-directional raster scan t1 indicates the start time of row number 1, t2 indicates the start time of the second row, and similarly for subsequent lines, where to indicate the begin time of nth-row scan. Simultaneously with the scan the laser is intensity modulated with respect to the video information of the camera. The video information associated with row #1 starts at t1 and ends at t1+T. The time t2−(t1+T) to beginning of raw #2 is "dead" time required for the scanner to re-position vertically to assume the raster scan of subsequent row. The plots on the left hand side in FIG. 12 show exemplary video signal according which the laser is intensity modulated. For each raw there corresponds a video signal. A typical image may include hundreds of raster rows, in the example only the first four rows are shown. Plots on the right hand side of FIG. 12 illustrate an example when the video signal corresponding originally to rows #3 and rows #4 is delayed and instead appears shifted to raw #5, while during the scan of rows #3 and #4 the laser is turned off. As the result of the introduced delay the original video signal that was corresponding to subsequent rows has also has been shifted by one row. It is noted that the video information of the last row will be omitted from the video frame. However the last row, or even a number of rows if the shift is more than one row, correspond to the peripheral of the field of vision and very often are less critical for vision related activities such as for example reading. Evaluating the best strategy for re-projecting and more precisely which rows are skipped depends largely on the severity of retinal degeneration at its central regions information which is stored in the RRST.

In stage 5, light is projected onto the retina according to the transformed video signals. Stages 3-5 are optionally and preferably repeated for each row or column of pixels for the transformed video signals, as necessary in order to project the entire image onto the retina.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An apparatus for aiding the vision of a visually impaired individual having a retina with reduced functionality by compensating for reduced and/or uneven retinal function, comprising a source of video data, a video processor constructed and arranged to process video frames projected by said source of video data according to a relative retinal sensitivity table (RRST) comprising amplification factors for each area of the retina, wherein two amplification factors have nonzero values that differ from each other; a bright collimated light source having an intensity, and scanning optics adapted to focus light from said light source onto a portion of the retina according to the RRST and according to said source of video data as determined by said video processor, said video processor further adapted to affect a light intensity and focus location on the retina according to said RRST, wherein affecting the light intensity comprises multiplying the intensity of the light signal by the respective value in the RRST and wherein affecting the focus location comprises focusing the light intended for a damaged area of the retina on another area of the retina; wherein said scanning comprises projection optics; and an optical scanner constructed and arranged to receive light from said light source and scan said light through said projection optics according to said RRST; said optical scanner comprising a horizontal scanner and a vertical scanner, for horizontal and vertical scanning of said light, respectively; wherein said projection optics comprise a scan mirror and a plurality of lenses for focusing light on a plurality of portions of said retina; and wherein said plurality of lenses comprise a first lens having a back focal plane coinciding with a pupil of the individual, a second lens having a back focal plane coinciding with a front focal plane of said first lens and a third lens constructed and arranged to provide fine tuning divergence of said light.

2. The apparatus of claim 1, wherein said light source comprises a plurality of light sources including at least a light source emitting red light, a light source emitting green light and a light source emitting blue light.

3. The apparatus of claim 2, further comprising collimation optics for each light source.

4. The apparatus of claim 2, wherein said light sources comprise one of laser diodes and light emitting diodes (LED).

5. The apparatus of claim 2, further comprising a beam combiner for combining light from said light sources to a single light beam.

6. The apparatus of claim 5, further comprising:
an intensity monitor for monitoring an intensity of said single light beam and for ceasing operation of said light sources if said intensity is higher than a maximum threshold; and
control electronics for controlling operation of said light sources and for receiving a shutoff signal from said intensity monitor if said intensity is higher than a maximum threshold,
wherein said intensity is different for each color of light and for each light source.

7. The apparatus of claim 1, further comprising an eye tracking system for determining a position of a pupil of the individual and for providing feedback to said video processor.

8. The apparatus of claim 1, wherein said video processor emits a modulation signal to said light source for controlling modulation of said light source.

9. The apparatus of claim 1, contained in two units; a first unit for mounting onto a head of the individual and a second unit for containing said video processor and said video source, wherein said first unit contains said light source, said optical scanner, said projection optics and an eye tracking system.

10. The apparatus of claim 1, wherein said optical scanner is a MEMS (micro-electro-mechanical systems) scanner.

11. The apparatus of claim 1, wherein said projection optics is constructed and arranged to project only part of a video frame across the entire field of view of the retina for achieving a larger magnification.

12. The apparatus of claim 1, wherein the amplification factors have sixteen levels.

* * * * *